United States Patent [19]

Watson

[11] 4,061,545

[45] Dec. 6, 1977

[54] POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[21] Appl. No.: 659,570

[22] Filed: Feb. 19, 1976

[51] Int. Cl.² .................... B01D 3/34; C07C 15/10
[52] U.S. Cl. ........................ 203/9; 203/49; 203/51; 203/58; 203/59; 203/65; 260/666.5; 260/669 A
[58] Field of Search ............ 203/9, 8, 49, 65, 38, 203/58, 51, 56, 59; 260/669 A, 666.5

[56]  References Cited

U.S. PATENT DOCUMENTS

| 2,388,041 | 10/1945 | Craig | 203/9 |
| 3,239,433 | 3/1966 | Costolon | 203/8 |
| 3,275,531 | 9/1966 | Sennewald et al. | 203/8 |
| 3,329,582 | 7/1967 | Sennewald et al. | 203/8 |
| 3,354,055 | 11/1967 | Sennewald et al. | 203/8 |
| 3,433,831 | 3/1969 | Yomiyama et al. | 203/8 |
| 3,666,794 | 5/1972 | Otsuki et al. | 203/8 |
| 3,763,015 | 10/1973 | Morimoto et al. | 203/9 |
| 3,794,567 | 2/1974 | Otsuki | 203/8 |
| 3,816,265 | 6/1974 | Daniels et al. | 203/59 |
| 3,933,599 | 1/1976 | Watson | 203/9 |

Primary Examiner—Wilbur L. Bascomb, Jr.

[57] ABSTRACT

Disclosed is a process for the distillation of readily polymerizable vinyl aromatic compounds which comprises subjecting such compounds to distillation conditions in the presence of an effective amount of a combination of phenothiazine and a phenolic compound, preferably tert-butylcatechol (TBC), as a polymerization inhibitor system in the presence of oxygen.

8 Claims, No Drawings

POLYMERIZATION INHIBITOR FOR VINYL AROMATIC COMPOUNDS

BACKGROUND OF THE INVENTION

The present invention relates to a process for the distillation of readily polymerizable vinyl aromatic compounds, and more especially, to a process for the distillation of styrene, substituted styrene, divinylbenzene, and mixtures thereof, wherein the amount of said materials polymerized during distillation is reduced over an extended period of time, wherein the material accumulating in the bottom or reboiler area of the distillation apparatus is essentially free from significant sulfur contamination, and wherein the rate of throughput for a given distillation apparatus may be increased over the rate at which such apparatus may be operated in accordance with conventional methods.

It is well known that vinyl aromatic compounds such as monomeric styrene, lower alkylated styrene, e.g., alpha-methyl styrene, and the like polymerize readily, and furthermore, that the rate of polymerization increases with increasing temperature. Inasmuch as vinyl aromatic compounds produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatic compounds under distillation conditions include 4-tert-butylcatecol (TBC) and hydroquinone. Additionally, sulfur has been widely employed as a polymerization inhibitor during the distillation of various vinyl aromatic compounds. However, while sulfur provides a reasonably effective inhibitor, its use in such distillation processes results in a highly significant disadvantage, namely, there is formed in the reboiler bottoms of the distillation column a valueless waste material highly contaminated with sulfur. This waste material furthermore represents the significant problem of pollution and/or waste removal.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any real utility for inhibiting vinyl aromatic polymerization under distillation conditions. In a typical distillation process for vinyl aromatic compounds utilizing a polymerization inhibitor, the mixture of vinyl aromatic material to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude styrene (a mixture containing, inter alia, styrene, ethyl benzene and tars) to obtain high purity styrene, even when inhibited with sulfur and TBC, a styrene product is obtained which contains significant quantities of polymer which are difficult to separate from the product and are detrimental to the end use of such styrenes. Furthermore, the material removed from the bottom or reboiler area of the distillation apparatus is a highly polluting sulfur-containing waste material which must be disposed.

Accordingly, there exists a strong need for a polymerization inhibitor which will effectively present the polymerization of vinyl aromatic compounds during distillation thereof, without the attendant problem of generating copious quantities of noxious waste.

SUMMARY OF THE INVENTION

It is therefore an object of the present invention to provide a new and improved process for the distillation of readily polymerizable vinyl aromatic compounds.

A further object of the present invention is to provide a new and improved process for the distillation of readily polymerizable vinyl aromatic compounds.

A further object of the present invention is to provide a new and improved process for the distillation of readily polymerizable vinyl aromatic compounds, which process results in higher recovery of high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet, another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is yet another object of the present invention to provide a new and improved process for the distillation of vinyl aromatic compounds which provide all of the foregoing enumerated advantages in an elevated temperature distillation process.

In accomplishing the foregoing and other objects, there has been provided in accordance with the present invention a process for the distillation of a readily polymerizable vinyl aromatic compound comprising subjecting the vinyl aromatic compound to distillation conditions in the presence of an effective amount of phenothiazine and a phenolic compound in the presence of oxygen to inhibit polymerization of the vinyl aromatic compound under the distillation conditions. Broadly, any phenolic compound may be used with the phenothiazine; however, tert-butylcatechol (TBC) is most preferred. In one aspect of the process according to the invention, the inhibitor is simply introduced into the distillation system by injection into the reboiler area of the distillation apparatus, or alternatively, by injection into the incoming stream of vinyl aromatic compound to be purified. It is one salient feature of the present invention that the mode of introducing and metering the amount of polymerization inhibitor is considerably simplified due to the ease of metering the material and due to the simplicity of the equipment necessary therefor, as the inhibitor material is soluble in solvents compatible with the styrene feed, including styrene itself.

The amount of phenothiazine and phenolic compound necessary to inhibit polymerization of the vinyl aromatic compounds may vary over a broad range depending upon various factors of the distillation process as, for example, temperature, amount of reflux, if any, pressure, residence time, etc. Typically, however, it has been found that an amount of inhibitor between about 5 ppm and 200 ppm of phenothiazine and between about 1 ppm and about 100 ppm of the phenolic compound is sufficient to substantially inhibit polymerization of vinyl aromatic compounds under normal distillation conditions, e.g., at about 115° C.

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Also, the rate of operation of a given distillation apparatus may be increased in proportion th the decrease in the amount of polymer formation. Also, the rate of operation of a given distillation apparatus may be increased over and above the rate of operation for the same apparatus utilizing conventional methods. Still further, the material accumulating in the bottom or reboiler area of the distillation apparatus can be reused, e.g., for its fuel value or for reprocessing, which is a distinct advantage over conventional methods utilizing sulfur as a polymerization inhibitor which methods produce a highly polluting waste material in the reboiler area. Furthermore, it has also been found that any polymeric material inadvertently formed during the process of the invention presents fewer problems with fouling of the distillation apparatus.

Further objects, features and advantages of the invention will become apparent from the detailed description which follows and from the claims.

DETAILED DESCRIPTION OF THE PREFERRED EMBODIMENT

The distillation process of the present invention employs phenothiazine in combination with a phenolic compound, preferably TBC, as a polymerization inhibitor during the distillation of vinyl aromatic compounds, especially styrene, for the purification thereof. The distillation process may be conducted over wide-ranging parameters including reduced pressure distillation (i.e., vacuum distillation) and atmospheric distillation (i.e., open to the atmosphere) and over a fairly broad range of temperatures, from about 65° to about 150° C. One of the most significant advantages of the invention, in addition to the broad operative ranges of pressure and temperature and the reduction of unwanted polymerization, is that the use of sulfur in the distillation system may be avoided, thus obviating the production of noxious by-products and the attendant problem of their disposal for further processing.

The primary inhibitor component of the present invention, phenothiazine, $C_{12}H_9NS$, as defined in the Condensed Chemical Dictionary, Seventh Edition, published by Van Nostrand Reinhold Company, is a grayish-green to green-yellow powder, granule or flake which is tasteless but with a slight odor. It is insoluble in ether and water but soluble in acetone. The melting point is between 175° and 185° C and the boiling point is 371° C.

The other component of the inhibitor system according to the invention is a phenolic compound. This class of materials is well known, and some of the more common types are represented by the formula

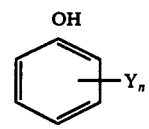

wherein Y is selected from the group of lower alkyl of from about 1 to 8 carbon atoms, hydroxyl, or lower alkoxy of about 1 to 8 carbon atoms, and n is a member of from 1 to 5. Preferably, there is at least one tertiary alkyl substituent on the ring, most preferably tertiary-butyl. The most preferred phenolic compound for use in conjunction with the phenothiazine in the inhibitor system of the invention is tertiary-butyl catechol (TBC). In many instances, the combined phenothiazine/phenolic compound inhibitor system may be further enhanced by incorporation of other known vinyl aromatic polymerization inhibitors, particularly nitroso diphenylamine (NDPA) in an amount of about 10 to 500 ppm, preferably from about 25 to 200 ppm based upon the vinyl aromatic compound.

The phenolic component is likewise soluble in the vinyl aromatic material. Accordingly, the inhibitor system of the invention may be added to the incoming stream of vinyl aromatic material, into the reboiler area of the distillation apparatus, or at other suitable points.

Other significant advantages are realized by employing the combined phenothiazine, phenolic inhibitor system of the present invention. Firstly, phenothiazine is relatively nontoxic as evidenced by various medicinal (veterinary) applications. Its efficiency, defined as molar ability to trap styryl radicals, is greater than 1 as compared with other conventional inhibitors having efficiencies ranging up to about 0.3. Significantly, also, the persistency of inhibiting effect, i.e., duration of effectiveness, is also substantially greater than prior art inhibitors, the phenothiazine being synergistic with TBC. Accordingly, these properties allow for use of relatively low loadings (about 25 to about 60 ppm phenothiazine with as little as about 10 ppm to about 50 ppm phenolic compound), relative to other known inhibitors. Consequently, while the sulfur constituent of the phenothiazine inhibitor (16 weight percent) will provide some slight amount of sulfur contamination, it has been determined that this is relatively inconsequential in commercial distillation processes. That is, employment of phenothiazine in a 600 million pound per year unit at a loading of 100 ppm relative to the vinyl aromatic product would result in the production of a mere 26.5 pounds per day of sulfur in the resulting tars. Balanced against the increased efficiency of phenothiazine/TBC as a polymerization inhibitor, it is manifestly apparent that such levels are not appreciable compared with, for example, sulfur as an inhibitor.

The distillation technique of the process of the present invention is suitable for use in virtually any type of distillative separation of a readily polymerization vinyl aromatic compound from a mixture wherein the vinyl aromatic compound is subjected to temperatures above room temperature. Surprisingly, the process of the present invention has been found adaptable to reduced pressure distillation techniques (vacuum distillation) as well as atmospheric distillation techniques (i.e., open to the atmosphere). In the event the reduced pressure method is employed, however, air or oxygen must be added to the system (e.g., feed stream) in order that the inhibitor exhibits efficacy. It is also possible to pre-mix by dispersion or the like the air or oxygen into the inhibitor system prior to adding the inhibitor.

The oxygen employed in combination with the phenothiazine in accordance with the present invention may be in the form of oxygen or an oxygen-containing gas. Of course, if an oxygen-containing gas is employed, the remaining constituents of the gas must be inert to the vinyl aromatic compounds under the distillation conditions. The most useful, practical and least expensive source of oxygen is, of course, air which is preferred for the present invention. The amount of oxygen employed may vary widely but generally will be approximately that found in air.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 5 and about 200 ppm phenothiazine in combination with about 1 ppm to about 100 ppm TBC have generally provided suitable results, depending primarily upon the temperature of the distillation mixture and the degree of inhibition desired.

During distillation of the vinyl aromatic mixtures, the temperature of the reboiler is preferably maintained from about 65° to about 150° C. Preferred, however, is a temperature within the range of from about 90° to about 143° C. Under such conditions, in a distillation apparatus having a distillation zone containing from about 50 to 100 distillation stages, inhibitor concentrations of from about 25 to about 100 ppm phenothiazine in combination with about 5 ppm to about 80 ppm phenolic compound is suitable, whereas concentrations of from about 25 to about 60 ppm phenothiazine in combination with about 20 ppm to about 50 ppm phenolic compound are preferred. Obviously, amounts of inhibitor greater than those specified hereinabove may be employed, although the advantages of adding the additional inhibitor are not significant and are outweighed by the corresponding increase in the cost.

The polymerization inhibitor of the present invention may be introduced into the distillation apparatus in any convenient manner which permits efficient distribution of the inhibitor throughout the apparatus. The inhibitor may be added to the incoming stream of styrenic material, into the reboiler area of the distillation column, or at any other convenient location.

Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittent charging inhibitor into the distillation system. The means by which the maintenance of the necessary inhibitor concentration is carried out is of no particular importance provided the concentration of inhibitor is maintained above the minimum required level.

Use of the polymerization inhibitor system of the present invention enables the distillation apparatus to operate at an increased rate as opposed to conventional prior art processes since the inhibitor of the present invention is more efficient than conventional inhibitors, and will thus permit higher distillation temperatures at higher pressures. In this manner, the rate of distillation may be increased without increasing the amount of polymerization which has been deemed to be acceptable in accordance with conventional distillation procedures.

When the process of the present invention is utilized, the bottoms material which accumulates during the distillation process can be drawn off and utilized for its heating value or for reprocessing. As the amount of sulfur contamination is relatively inconsequential, this represents another significant advantage in comparison to conventional processes for distillation of vinyl aromatic compounds which employ sulfur as the polymerization inhibitor, or sulfur in combination with other chemical polymerization inhibitors.

Upon recovery of the distillation product obtained from the process of the present invention, it is found that a higher percentage of the pure readily polymerizable vinyl aromatic compound is recovered in an unpolymerized state, and that the inhibitor employed does not derrogate from the ability of the recovered monomer to undergo subsequent polymerization. Furthermore, it has been noted that the polymeric products which are formed during the distillation process of the invention are of such a character that there is less fouling or plugging of the apparatus as compared with many conventional inhibitors.

In order to more fully describe the present invention, the following examples are presented which are intended to be merely illustrative and not in any sense limitative of the invention.

EXAMPLE 1

Three 100 ml. reaction flasks are prepared: A first (1) is charged with 50 grams distilled styrene, having no TBC content, to which is added 100 ppm phenothiazine; a second (2) being charged with 50 grams of finished styrene containing approximately 8 ppm TBC; and a third (3) being charged with 50 grams distilled styrene to which is added 10 ppm TBC and 100 ppm phenothiazine. Each of these flasks is fitted with a magnetic stirrer and septum closures and heated in a stirred oil bath to 115° C., ± 1° C.

Samples are removed periodically from each of the reaction flasks through a hypodermic syringe and tested for turbidity with methanol. The following results are obtained:

TABLE I

| Sample | Duration of Inhibition (hours) |
| --- | --- |
| 1 | 1.0 – 1.5 |
| 2 | less than 0.5 |
| 3 | 4.0 – 4.5 |

Accordingly, it is observed from the foregoing data that neither TBC nor phenothiazine alone is capable of providing the degree of inhibition observable when employed conjunctively; that is, phenothiazine and TBC are synergistic as a styrene polymerization inhibitor.

EXAMPLE 2

Four reaction flasks are prepared as in Example 1, each being charged with 50 grams of distilled styrene having no inherent TBC content. To the first flask (1) is added 25 ppm phenothiazine and 10 ppm TBC; to the second (2) is 25 ppm phenothiazine and 20 ppm TBC; to the third (3) is added 50 ppm phenothiazine and 10 ppm TBC; and, to the fourth (4) is added 50 ppm phenothiazine and 40 ppm TBC, this being a 1:1 molar ratio. Each of these reaction flasks is heated in a stirred oil bath to 115° C., ± 1° C., and samples are periodically withdrawn for turbidity testing with methanol. The following results are obtained:

TABLE II

| Sample | Duration of Inhibition (hours) |
|---|---|
| 1 | 1.5 – 2.0 |
| 2 | about 2.0 |
| 3 | 2.5 – 3.0 |
| 4 | greater than 8.0 |

Thus, it is observable that the optimum relative amounts of the phenothiazine and TBC components is a 1:1 molar ratio.

EXAMPLE 3

A 12-inch diameter distillation column is packed with pro-pac column packing (a commercially available stainless steel packing manufactured by Scientific Design Company). The column is provided with continuous feed of neat styrene and continuous overhead draw; bottoms being drawn hourly to maintain the reboiler level. The column is charged with the monomeric styrene and a continuous feed of 400 ml/min. to account for a residence time of approximately 6.3 hours. The steam jacket is suitably heated to maintain an average reboiler temperature of 221° F (105° C.). Reflex ratio was varied over the range 3:1 to 20:1. An inhibitor of 50 ppm phenothiazine and 30 ppm TBC is added to the incoming feed of styrene, which contains about 10 ppm TBC, to yield a desired 1:1 molar ratio of constituents. Air injection is established at 1.2 l/min. to the reboiler base. After 7.5 hours the air injection is increased to 2.0 l/min. After 14.5 hours the inhibitor concentration added to the feed is increased to 75 ppm phenothiazine and 45 ppm TBC. Steady-state is attained after approximately 18 hours and the test is allowed to proceed for a total approximate time of 23.5 hours. Bottoms are withdrawn periodically during the test and concentrated to dryness by rotary evaporation to determine the percent polymer content. While operating at steady state conditions, the viscosity of the reboiler liquid is tested with a Brookfield viscometer: a viscosity of 0 is observed. At the termination of the run, it is found that only 7.2% polymer is present. The results of this run are summarized in the following Table:

TABLE III

| Elapsed Time (hrs.) | Reboiler Temp. (° F.) | Phenothiazine/TBC Inhibitor Added to Feed (ppm) | Air Injection (l/min) | % Evaporation Residue |
|---|---|---|---|---|
| 0.5 | 196 | 50/30 (added) | 1.2 | — |
| 1.0 | 211 | " | " | 0.3 |
| 1.5 | 220 | " | " | 0.2 |
| 2.5 | 223 | " | " | 0.3 |
| 3.5 | 224 | " | " | 0.5 |
| 4.5 | 222 | " | " | 0.7 |
| 5.5 | 222 | " | " | 2.4 |
| 6.5 | 224 | " | " | 2.9 |
| 7.5 | 223 | " | 2.0 | 4.0 |
| 8.5 | 221 | " | " | 3.1 |
| 9.5 | 223 | " | " | 4.5 |
| 10.5 | 226 | " | " | 4.1 |
| 11.5 | 221 | " | " | 5.2 |
| 12.5 | 220 | " | " | 3.4 |
| 13.5 | 221 | " | " | 4.9 |

TABLE III-continued

| Elapsed Time (hrs.) | Reboiler Temp. (° F.) | Phenothiazine/TBC Inhibitor Added to Feed (ppm) | Air Injection (l/min) | % Evaporation Residue |
|---|---|---|---|---|
| 14.5 | 223 | 75/45 (added) | " | 7.0 |
| 15.5 | 220 | " | " | 8.8 |
| 16.5 | 220 | " | " | 9.4* |
| 17.5 | 220 | " | " | 9.3* |
| 18.5 | 220 | " | " | 9.6* |
| 19.5 | 221 | " | " | 8.7* |
| 20.5 | 221 | " | " | 8.8* |
| 21.5 | 220 | " | " | 8.1 |
| 22.5 | 220 | " | " | 7.8 |
| 23.5 | 220 | " | " | 7.2 |

*Viscosity = 0

EXAMPLE 4

In order to ascertain the minimum air addition rate to permit effective utilization of the inhibitor of the present invention, a distillation column as described in Example 3 is prepared. The reboiler temperature is maintained at an average of 221° F and the inhibitor addition to the feed is maintained at 75 ppm phenothiazine and 45 ppm TBC (added), while the air injection rate was varied from 2.0 l/min. to 0 and then re-established at 0.50 l/min. The test is conducted over approximately 23 hours and bottoms are drawn periodically and concentrated to indicate percentage residue indicative of polymer formation. The results of this run are summarized in the following Table.

TABLE IV

| Elapsed Time (hrs.) | Air Injection Rate (l/min.) | Evaporation Residue (%) |
|---|---|---|
| 0 | 2.0 | — |
| 1 | 2.0 | 0.2 |
| 3.5 | 2.0 | 1.4 |
| 8.0 | 2.0 | 2.3 |
| 9.0 | 2.0 | 2.6 |
| 10.0 | 1.0 | 2.8 |
| 11.0 | 1.0 | 3.1 |
| 12.0 | 1.0 | 3.3 |
| 13.0 | 1.0 | 3.5 |
| 14.0 | 0.55 | 4.2 |
| 15.0 | 0.50 | 4.5 |
| 16.0 | 0.25 | 4.2 |
| 17.0 | 0.25 | 4.2 |
| 18.0 | 0.25 | 4.3 |
| 19.0 | 0.25 | 4.6 |
| 19.25 | 0 | * |
| 20.0 | 0 | 6.6 |
| 20.1 | 0.50 | * |
| 21.0 | 0.50 | 7.4 |
| 22.0 | 0.50 | 6.7 |
| 23.0 | 0.50 | 5.8 |

*No Sample Taken

EXAMPLE 5

NDPA (nitroso diphenylamine) is employed as a polymerization inhibitor under the same conditions outlined in Example 3, save for the flow rate of the styrene feed, which is varied below that of Example 3. The inhibitor is added to the incoming feed in an amount of 400 ppm. Bottoms are periodically withdrawn and viscosity measurements made with a Brookfield viscomiter at 70° F. Similarly, bottoms are concentrated by evaporation to indicate percent polymer formation. The results of this run are summarized in the following Table.

TABLE V

| Elapsed Time (hrs.) | Reboiler Temp. (° F.) | Styrene Feed (ml/min.) | Viscosity at 70° F. CP | Evaporation Residue % |
|---|---|---|---|---|
| 0 | 86 | — | — | — |
| 1.5 | 218 | — | — | — |

TABLE V-continued

| Elapsed Time (hrs.) | Reboiler Temp. (° F.) | Styrene Feed (ml/min.) | Viscosity at 70° F. CP | Evaporation Residue % |
|---|---|---|---|---|
| 2.0 | 220 | 225 | — | — |
| 3.0 | 222 | 225 | 0 | — |
| 5.0 | 221 | 230 | 0 | 5.4 |
| 7.0 | 220 | 230 | 0 | 12.2 |
| 8.0 | 220 | 320 | 20 | * |
| 9.0 | 219 | 320 | 40 | 17.0 |
| 11.0 | 221 | 320 | 56 | 19.3 |
| 15.0 | 221 | 320 | 48 | 18.7 |
| 17.0 | 221 | 320 | 44 | 18.9 |
| 19.0 | 221 | 320 | 44 | 19.4 |
| 21.0 | 221 | 320 | 40 | 18.4 |
| 24.0 | 221 | 320 | 40 | 15.6 |

* No Sample Taken

Comparison of Examples 3 and 5 serves to demonstrate the severity of the test performed and the surprising and unexpected results obtainable by the present invention.

EXAMPLE 6

A distillation column is prepared as outlined in Example 3. The feed to this column is synthetic crude styrene comprised of 60% styrene and 40% ethylbenzene. Both the amount of inhibitor and volume flow rate of air added are varied over the course of the test, which is conducted for approximately 70 hours, with an approximate 6.3 hour residence to provide the attainment of true steady-state conditions. Bottoms are periodically withdrawn and evaporation residue recorded. The results of this run are summarized in the following table.

TABLE VI

| Elapsed Time (hrs.) | Reboiler Temp. (° F.) | Pheno./TBC (ppm) | Air Injection (ml/min.) | Evaporation Residue (%) |
|---|---|---|---|---|
| 0 | 152 | 75/45[1](125/75)[2] | 0.5 | — |
| 0.5 | 217 | " | 0.6 | — |
| 1.75 | 221 | " | 0.5 | 0.8 |
| 2.75 | 221 | " | " | 0.5 |
| 3.25 | 216 | 45/27(75/45) | " | * |
| 3.75 | 219 | " | " | 0.3 |
| 4.75 | 222 | " | " | 0.2 |
| 5.75 | 223 | " | " | 0.2 |
| 6.25 | 223 | 30/18(50/30) | 0.25 | — |
| 6.75 | 223 | " | " | 0.3 |
| 7.75 | 222 | " | " | 0.3 |
| 8.75 | 221 | " | " | 0.5 |
| 9.75 | 221 | " | " | 0.8 |
| 14.75 | 220 | " | " | 0.9 |
| 22.75 | 220 | " | " | 1.2 |
| 25.75 | 219 | " | " | 2.4 |
| 26.75 | 219 | " | " | 2.3 |
| 30.75 | 222 | " | " | 1.0 |
| 32.75 | 222 | " | " | 0.8 |
| 38.75 | 221 | " | " | 0.8 |
| 45.75 | 221 | " | " | 0.14 |
| 49.0 | — | 30/9 (50/15) | " | 0.14 |
| 50.75 | 220 | " | " | 0.5 |
| 55.75 | 221 | " | " | 0.6 |
| 58.75 | 221 | " | " | 0.7 |
| 60.75 | 222 | " | " | 0.9 |
| 62.75 | 220 | " | " | 0.9 |
| 66.75 | 219 | " | " | 0.5 |
| 69.75 | 221 | " | " | 0.3 |

[1]Relative to Feed
[2]Relative to Styrene

EXAMPLE 7

A 100 ml. reaction flask is charged with 50 grams of finished styrene containing approximately 8 ppm TBC, to which is added 50 ppm phenothiazine, 25 ppm TBC, and 150 ppm NDPA relative to the weight of the styrene. The flask is fitted with a magnetic stirrer and a septum closure and heated in a stirred oil bath to 115° C., ±1° C. Samples are periodically removed from the flask through a hypodermic syringe and tested for turbidity upon methanol dilution. The results indicate a lack of turbidity (i.e., clear specimen) over a period of eight hours.

While the invention has been described in terms of various preferred embodiments and illustrated by numerous examples, the skilled artisan will appreciate that various modifications, substitutions, omissions, and changes may be made without departing from the spirit thereof. Thus, for example, the TBC component might be replaced by a known phenolic compound, e.g., butylated hydroxytoluene (BHT) or butylated hydroxyanisole (BHA) without departing from the scope of the present invention, albeit TBC is the most preferred of these materials. Accordingly, it is intended that the scope of the present invention be limited solely by the scope of the following claims.

What is claimed is:

1. A process for the distillation of a readily polymerizable vinyl aromatic compound selected from the group consisting of styrene, substituted styrene, divinylbenzene and mixtures thereof, which comprises subjecting said compound to distillation conditions in the presence of an effective amount of a combination of phenothiazine ($C_{12}H_9NS$) and tertiarybutylcatechol (TBC) as a polymerization inhibitor system in the presence of oxygen.

2. The process of claim 1, wherein said inhibitor system is continuously added to said vinyl aromatic compound.

3. The process of claim 1, wherein said vinyl aromatic compound comprises styrene.

4. The process of claim 1, wherein said inhibitor system is present in an amount of from about 5 ppm to about 200 ppm phenothiazine and from about 1 ppm to about 100 ppm TBC.

5. The process of claim 1, wherein said distillation conditions comprise a temperature between about 65° and 150° C.

6. The process of claim 1, wherein said temperature is between about 90° and 143° C.

7. The process of claim 2, wherein said oxygen is supplied by air continuously added to said vinyl aromatic compound.

8. The process of claim 1, wherein said polymerization system further comprises nitroso diphenylamine.

* * * * *